United States Patent [19]

Siczek et al.

[11] Patent Number: 4,979,202
[45] Date of Patent: Dec. 18, 1990

[54] SUPPORT STRUCTURE FOR X-RAY IMAGING APPARATUS

[76] Inventors: Aldona A. Siczek; Bernard W. Siczek, both of 1252 Chinook Way, Boulder, Colo. 80303

[21] Appl. No.: 398,834

[22] Filed: Aug. 25, 1989

[51] Int. Cl.⁵ .............................................. H05G 1/02
[52] U.S. Cl. .................................. 378/198; 378/193; 378/196; 378/197
[58] Field of Search ............... 378/193, 195, 196, 197, 378/198, 11, 177, 189

[56] References Cited

U.S. PATENT DOCUMENTS 4,716,581 12/1987 Barod .................................. 378/198
4,866,752 9/1989 Bock et al. ........................... 378/198

Primary Examiner—Carolyn E. Fields
Assistant Examiner—David P. Porta

[57] ABSTRACT

A support structure for an X-ray imaging apparatus including an X-ray source and an X-ray receptor supported on opposite ends of a C-arm structure or the like is disclosed. This support structure provides a movement of a C-arm structure or the like a lengthwise and around a patient table allowing for examinations a patient's head side.

10 Claims, 2 Drawing Sheets

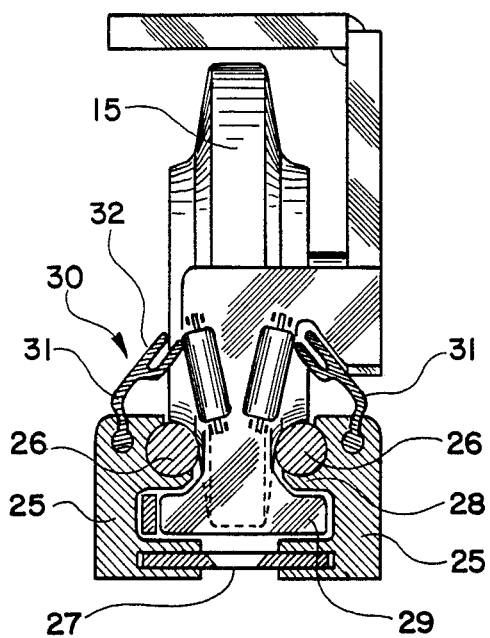
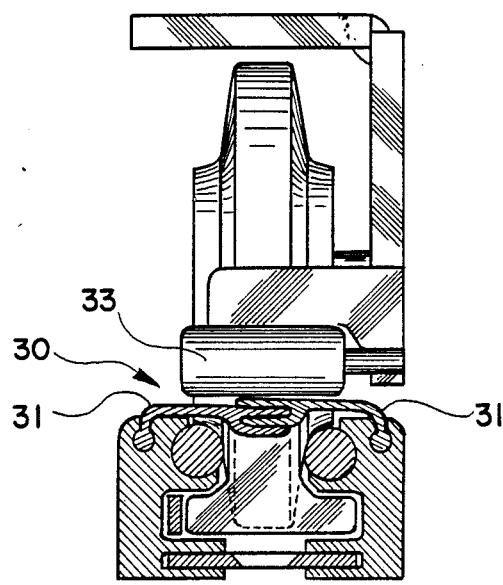
Fig. 3-A
Fig. 3-B
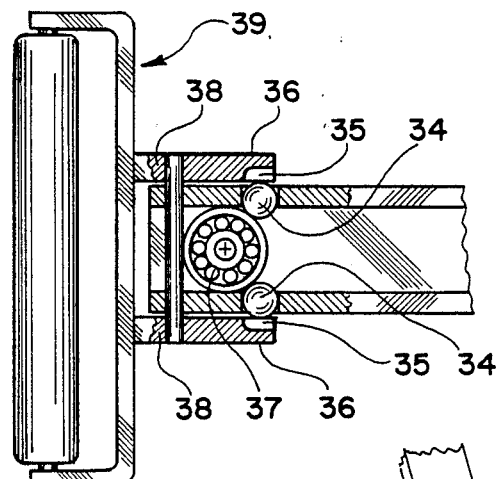
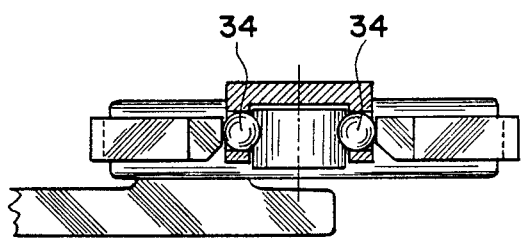
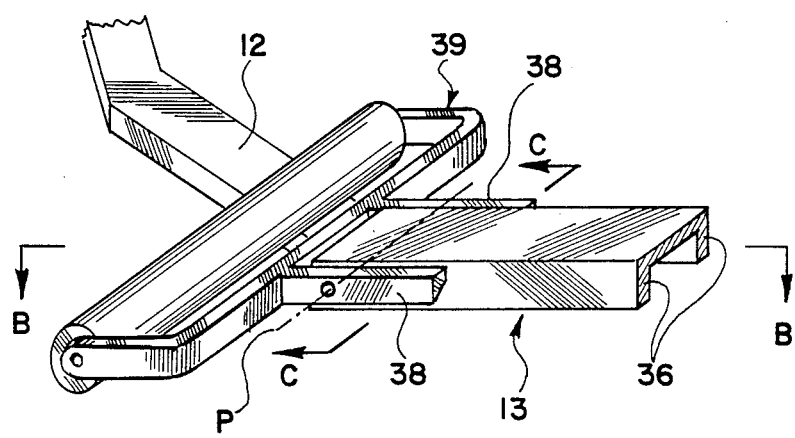
Fig. 4-B
Fig. 4-C
Fig. 4-A

SUPPORT STRUCTURE FOR X-RAY IMAGING APPARATUS

FIELD OF INVENTION

This invention relates to a support construction for an X-ray imaging apparatus including an X-ray tube and an image intensifier respectively mounted on opposite ends of a C-arm structure (or the like) and, more particularly, relates to a vascular system for effecting movement of the C-arm structure (or the like) lengthwise and around a patient-table.

BACKGROUND OF INVENTION

The use of an X-ray imaging apparatus including an X-ray tube and an image intensifier mounted on a C-arm structure or the like in general diagnostic procedures as well as in dedicated cardiac and/or vascular procedures is well known. However, improvements in various support constructions for effecting needed movement of the C-arm structure or the like are deemed to be useful in many applications. In particular now well known X-ray apparatus fails to provide adequate imaging coverage of a patient and does not permit examination from the patient's head side.

SUMMARY OF INVENTION

This invention provides a construction and a device, a combination of, for effecting a movement of a C-arm structure or the like having an X-ray source and an X-ray receptor mounted thereon, which movement is lengthwise and around a patient table.

It is therefore an object of this invention to provide a support construction for supporting the C-arm structure or the like to be moveable lengthwise and around the patient table.

It is another object of this invention to provide an X-ray imaging apparatus which provides complete imaging coverage of a patient.

It is still another object of this invention to provide an X-ray imaging apparatus which apparatus allows for a bi-plane examinations.

BRIEF DESCRIPTION OF THE DRAWINGS

The accompanying drawings illustrate a presently preferred embodiment of the invention according to the mode so far devised for the practical application of the principles thereof, and in which:

FIG. 3 is a cross section through a line A—A of FIG. 2 to illustrate the support rail and a device for covering same.

FIG. 4 illustrates the overhanging arm.

DESCRIPTION OF THE DRAWINGS

Figure 1:
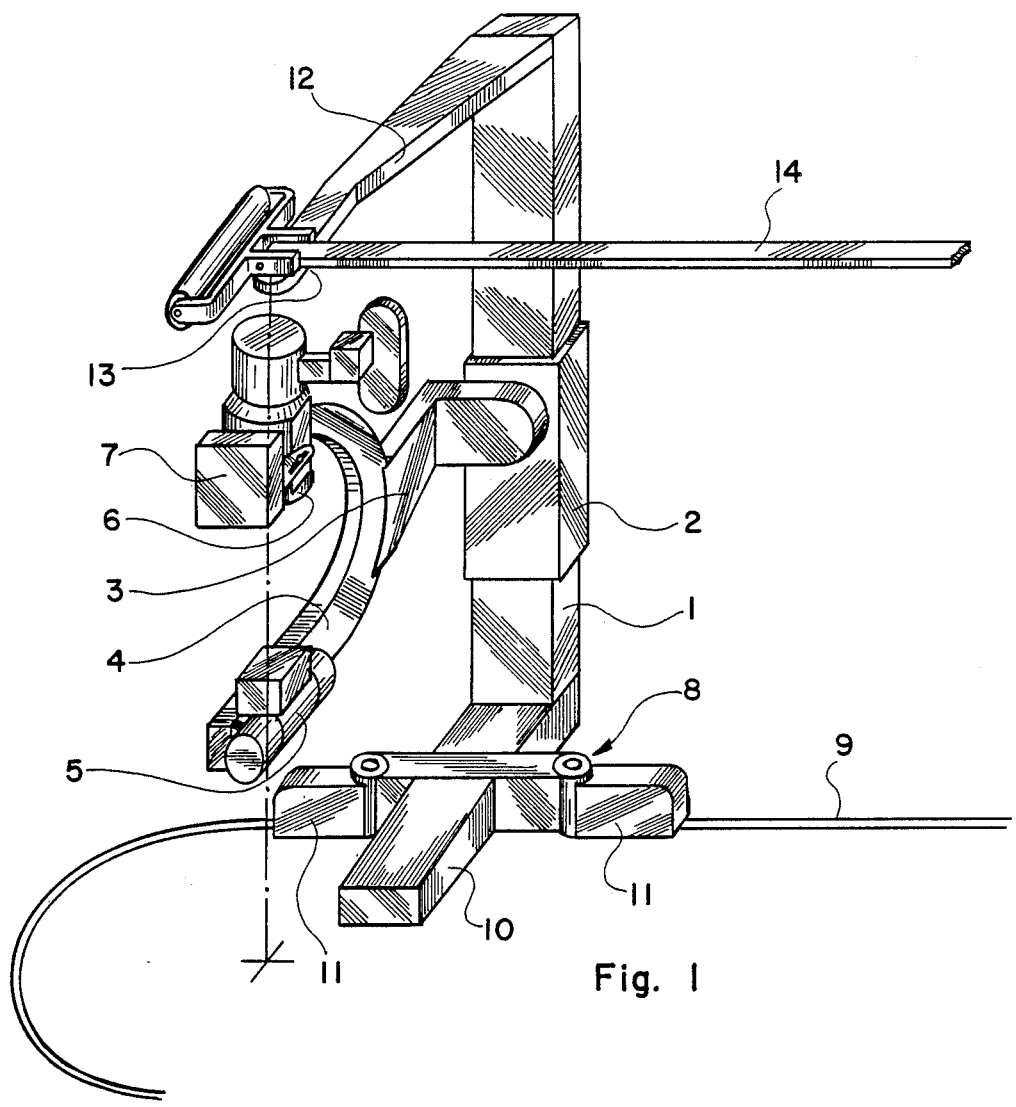
FIG. 1 is an isometric view of a C-arm X-ray imaging system mounted on a vertically extending support which support is supported from a ceiling by an overhanging arm following a guide rail and rests on a base moveable following the support rail disposed lengthwise, adjacent to and around a patient-table.

Shown in FIG. 1 is an X-ray imaging apparatus comprising an arc structure 4 supporting an X-ray tube 5 and an image intensifier 6 with a film changer 7 respectively disposed on two opposite extremities of thereof, wherein the arc structure 4 is secured to an arm member 3 which member is mounted on a sliding member 2 wherein the sliding member 2 is mounted on a vertically extending support structure 1 in a slideable relationship therebetween. The vertically extending structure 1 is secured to a base 8 moveable following a support rail 9 disposed lengthwise adjacent to and around a patient-table (not shown) and has an overhanging member 12 secured to an upper extremity thereof and pivotably supported at an overhanging extremity which extremity is slideable along a guide rail 14 disposed above the support rails 9 and retained by retainer means 13 while the overhanging member 12 pivots around the patient table. This overhanging member is curved on a plane generally perpendicular to a plane including said support rail.

The base 8 comprises a first member 10 extending horizontally in a direction generally perpendicular to the support rails 14 and secured to said vertically extending support and a pair of second members 11 respectively extending from the first member 10 in direction generally parallel to said support rails.

Figure 2:
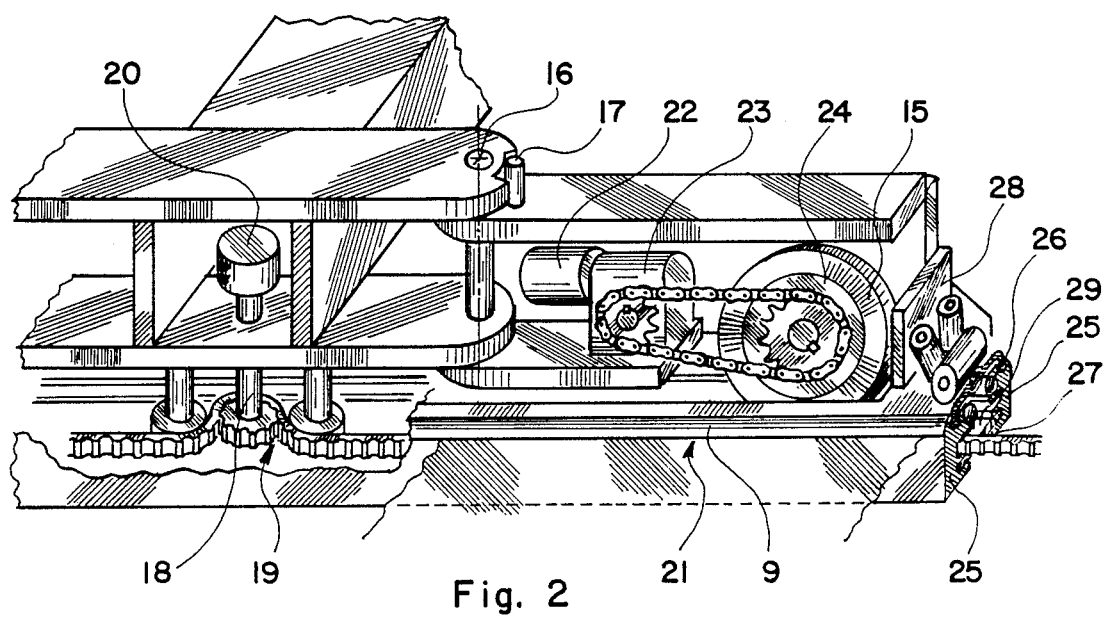
FIG. 2 illustrates the base and a drive means for the base in some detail.

As shown in FIG. 2 an extremity of each of the pair of second members 11 includes a roller 15 following the support rail 9 and said extremity is pivotably connected to a section secured to the first member 10 by means of a pin 16 and pivoting relative to this section in a range limited by means of a groove and a pin arrangement 17 to a small angle allowing the movement of the roller 15 around the patient-table (not shown).

A means for indicating a position of the apparatus relative to the support rails 9 are disposed in the base 8 and comprises: a vertically extending axle 18, a rotating means 19 whereby the rotating means rotates the axle 18 while the base is being displaced and a sensing means 20 for sensing said rotation movement.

A drive means 21 for the base 8 includes a motor 22 with a worm gear reducer 23 which means imparts driving motion to the roller 15 by means of a sprocket and chain arrangement 24. However, it is alternatively possible to connect the axle 20 with a drive imparting means (such as an electric motor with a reducer) whereby eliminating a need for the drive means 21 and the roller 15.

As shown in FIG. 2 and FIG. 3 the support rail 9 comprises a pair of elongated rail members 25, each of which includes a wire member 26 disposed on a rolling surface therein, and a horizontal plate 27 connecting the elongated rail members 25 by means of adhesive and forming a groove. To prevent the roller 15 from separating from the rail support 9 the roller has a tapered rim and also the rail support includes a flange 28 slideably engaged by a retainer member 29 affixed to the base 8.

FIG. 3 also shows a covering means 30 for protecting the rail support from dust, which covering means includes a pair of flexible elongated members 31 respectively attached at one end to the support rail 9 on the opposite sides of its groove, wherein overhanging ends of said pair of the elongated members includes means removeably coupling the overhanging ends with one another, whereby the covering means becomes open by the roller 15 by means of opening members 32 and closes in regions away from the roller 15 by means of a closing member 33.

As shown in FIG. 4 the retainer means 13 comprises a pair of balls 34, each of which is respectively disposed in an opening 35 extending across side walls 36 of the rail guide 14 allowing a bearing 37 mounted on the overhanging extremity 12 to slide to an end of the rail guide 14, a pair of pivoting members 38 pivotably mounted on said rail guide and pivoting around pivoting axis P, and further connected to a weight member 39 whereby this weight member is lifted by pivotal action of the overhanging 12 causing the pivoting members 38 to extend inward presses on the balls 34 and hence prevent the bearing 37 from sliding along the rail guide while allowing said pivotal movement.

What is claimed is:

1. A supporting apparatus including: a C-arm supporting an X-ray source and an X-ray image receptor respectively disposed on two opposite extremities of said C-arm, said C-arm being slideably mounted on a vertically extending support; a base moveable following a support rail disposed lengthwise adjacent to and around at least a portion of a patient-table; and a drive means for moving said base.

2. Apparatus according to claim 1 wherein said base comprises a first member extending horizontally in a direction generally perpendicular to the support rail and secured to said vertically extending support and a pair of second members respectively extending from said first member in directions generally parallel to said support rail wherein an extremity of each of said pair of second members includes a roller following the support rail.

3. Apparatus of the claim 2 wherein said extremity of each of said pair of the second members is pivotable relative to a section secured to said first member about an axis generally perpendicular to a plane including said support rail wherein pivoting motion between said extremity and said section secured to said first member is limited to a angle allowing the movement of the roller following the support rail.

4. Apparatus according to claim 2 wherein said base includes a means for indicating a position thereof relative to said support rail.

5. Apparatus according to claim 2 wherein said drive means includes a roller following a groove included in the support rail, said roller having a tapered rim and said groove having a tapered cross section whereby said groove guides said roller.

6. Apparatus according to claim 1 wherein said support rails comprises a pair of elongated rail members, each of which includes a wire member disposed on a rolling surface therein, a horizontal plate member connecting said elongated rail members and binding said members by adhesive.

7. Apparatus according to claim 5 wherein said support rail includes a covering member that becomes open by said roller and closes in regions away from said roller.

8. Apparatus of claim 7 wherein said covering member includes a pair of flexible elongated members respectively attached at one end to said support rail on opposite sides of said groove wherein overhanging edges of said pair of flexible elongated members includes means removeably coupling the overhanging ends to one another whereby said covering member becomes open by said roller and closes in regions away from said roller.

9. Apparatus according to claim 1 wherein said vertically extending support has an overhanging member secured to an upper extremity thereof and pivotably supported at an overhanging extremity by a retainer means, and further slideable along a guide rail disposed above the support rail, whereby said retainer prevents said overhanging member from sliding along the guide rail while allowing for pivotal movement of said member.

10. Apparatus according to claim 1 wherein said apparatus includes an overhanging member secured to an upper extremity of said vertically extending support, wherein said overhanging member is curved on a plane generally perpendicular to a plane including said support rail and is pivotably supported at an overhanging extremity thereof by a retainer means slideable along a guide rail disposed above the support rail.

* * * * *